(12) United States Patent
Eller et al.

(10) Patent No.: US 11,707,370 B2
(45) Date of Patent: Jul. 25, 2023

(54) STENTS AND RELATED METHODS

(71) Applicant: Merit Medical Systems, Inc., South Jordan, UT (US)

(72) Inventors: Zeke Eller, Plano, TX (US); Thomas Patrick Robinson, Addison, TX (US); Bryan K. Elwood, Arlington, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 398 days.

(21) Appl. No.: 16/994,260

(22) Filed: Aug. 14, 2020

(65) Prior Publication Data

US 2020/0375768 A1 Dec. 3, 2020

Related U.S. Application Data

(63) Continuation of application No. 15/921,172, filed on Mar. 14, 2018, now Pat. No. 10,744,009.
(Continued)

(51) Int. Cl.
*A61F 2/90* (2013.01)
*D04C 1/06* (2006.01)
(Continued)

(52) U.S. Cl.
CPC .................. *A61F 2/90* (2013.01); *D04C 1/02* (2013.01); *D04C 1/06* (2013.01); *D04C 3/48* (2013.01); *A61F 2210/0014* (2013.01); *A61F 2230/001* (2013.01); *A61F 2230/0078* (2013.01); *A61F 2240/001* (2013.01); *A61F 2250/0017* (2013.01); *A61F 2250/0023* (2013.01);
(Continued)

(58) Field of Classification Search
CPC ...... A61F 2/86; A61F 2/88; A61F 2/90; A61F 2002/041; A61F 2002/045; A61F 2230/001; A61F 2230/0017; A61F 2230/0065; A61F 2230/0076; A61F 2230/0078

See application file for complete search history.

(56) References Cited

U.S. PATENT DOCUMENTS 3,115,138 A 12/1963 McElvenny et al.
3,875,941 A 4/1975 Adair
(Continued)

FOREIGN PATENT DOCUMENTS

CN 210185778 3/2020
DE 9209908 U1 9/1992
(Continued)

OTHER PUBLICATIONS

European Examination Report dated Apr. 26, 2021 for EP11846358.7.
(Continued)

*Primary Examiner* — Brian A Dukert
(74) *Attorney, Agent, or Firm* — Dorsey & Whitney LLP

(57) ABSTRACT

Stents are disclosed herein. In some embodiments stents within the scope of this disclosure may comprise a first flared end and second flared end. In some embodiments, a profile of each of the first flared end and the second flared end may circumscribe a portion of separate elliptical arcs. In some embodiments, the stents are formed from braided or woven wires having a constant pitch along a middle region and continuously varying pitches along the first flared end and the second flared end. Methods of manufacturing stents are disclosed herein. Methods of using stents are also disclosed herein.

15 Claims, 9 Drawing Sheets

Related U.S. Application Data

(60) Provisional application No. 62/471,746, filed on Mar. 15, 2017.

(51) Int. Cl.
  *D04C 1/02* (2006.01)
  *D04C 3/48* (2006.01)

(52) U.S. Cl.
  CPC ................ *A61F 2250/0098* (2013.01); *D10B 2401/046* (2013.01); *D10B 2509/06* (2013.01)

(56) References Cited

U.S. PATENT DOCUMENTS

| | | | |
|---|---|---|---|
| 3,991,763 A | 11/1976 | Genese |
| 4,029,095 A | 6/1977 | Pena |
| 4,122,851 A | 10/1978 | Grossner |
| 4,139,130 A | 2/1979 | Glusker et al. |
| 4,265,381 A | 5/1981 | Muscatell |
| 4,429,693 A | 2/1984 | Blake et al. |
| 4,435,171 A | 3/1984 | Goldberg et al. |
| 4,511,358 A | 4/1985 | Johnson, Jr. et al. |
| 4,529,402 A | 7/1985 | Weilbacher et al. |
| 4,569,674 A | 2/1986 | Phillips et al. |
| 4,582,508 A | 4/1986 | Pavelka |
| 4,583,972 A | 4/1986 | Hunter, III et al. |
| 4,642,088 A | 2/1987 | Gunter |
| 4,666,432 A | 5/1987 | McNeish et al. |
| 4,850,955 A | 7/1989 | Newkirk |
| 4,904,245 A | 2/1990 | Chen et al. |
| 4,913,141 A | 4/1990 | Hillstead |
| 4,981,474 A | 1/1991 | Bopp et al. |
| 5,019,059 A | 5/1991 | Goldberg et al. |
| 5,067,950 A | 11/1991 | Broadnax, Jr. |
| 5,087,251 A | 2/1992 | Heyman et al. |
| 5,201,757 A | 4/1993 | Heyn et al. |
| 5,313,938 A | 5/1994 | Garfield et al. |
| 5,413,575 A | 5/1995 | Haenggi |
| 5,425,719 A | 6/1995 | Lessing, Jr. |
| 5,472,325 A | 12/1995 | Svendsen |
| 5,496,299 A | 3/1996 | Felix et al. |
| 5,534,007 A | 7/1996 | Germain et al. |
| 5,591,172 A | 1/1997 | Bachmann et al. |
| 5,591,196 A | 1/1997 | Marin et al. |
| 5,603,698 A | 2/1997 | Roberts et al. |
| 5,645,559 A | 7/1997 | Hachtman et al. |
| 5,733,325 A | 3/1998 | Robinson et al. |
| 5,735,301 A | 4/1998 | Rower |
| 5,755,769 A | 5/1998 | Richard et al. |
| 5,759,186 A | 6/1998 | Bachmann et al. |
| 5,824,041 A | 10/1998 | Lenker et al. |
| 5,868,755 A | 2/1999 | Kanner et al. |
| 5,876,448 A | 3/1999 | Thompson et al. |
| 5,916,147 A | 6/1999 | Boury |
| 5,944,727 A | 8/1999 | Ahari et al. |
| 5,968,052 A | 10/1999 | Sullivan, III et al. |
| 5,980,499 A | 11/1999 | Ekey |
| 6,015,429 A | 1/2000 | Lau et al. |
| 6,093,194 A | 7/2000 | Mikus et al. |
| 6,099,511 A | 8/2000 | Devos et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,261,276 B1 | 7/2001 | Reitsma |
| 6,270,524 B1 | 8/2001 | Kim |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,443,980 B1 | 9/2002 | Wang et al. |
| 6,447,531 B1 | 9/2002 | Amplatz |
| 6,461,319 B1 | 10/2002 | Ekey |
| 6,514,261 B1 | 2/2003 | Randall et al. |
| 6,520,983 B1 | 2/2003 | Colgan et al. |
| 6,530,933 B1 | 3/2003 | Yeung et al. |
| 6,574,800 B1 | 6/2003 | Leger et al. |
| 6,599,296 B1 | 7/2003 | Gillick et al. |
| 6,599,308 B2 | 7/2003 | Amplatz |
| 6,610,032 B1 | 8/2003 | Prody |
| 6,613,079 B1 | 9/2003 | Wolinsky et al. |
| 6,616,675 B1 | 9/2003 | Evard et al. |
| 6,620,132 B1 | 9/2003 | Skow |
| 6,629,981 B2 | 10/2003 | Dennis et al. |
| 6,645,143 B2 | 11/2003 | Mantassel et al. |
| 6,669,719 B2 | 12/2003 | Wallace et al. |
| 6,726,712 B1 | 4/2004 | Raeder-Devens et al. |
| 6,740,068 B1 | 5/2004 | Aruffo et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,887,223 B2 | 5/2005 | Bisbee |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,335,224 B2 | 2/2008 | Ohlenschaeger |
| 7,393,357 B2 | 7/2008 | Stelter et al. |
| 7,473,271 B2 | 1/2009 | Gunderson |
| 7,591,848 B2 | 9/2009 | Allen |
| 7,637,942 B2 | 12/2009 | Mangiardi et al. |
| 7,661,152 B2 | 2/2010 | Manzano-Rivera |
| 7,731,654 B2 | 6/2010 | Mangiardi et al. |
| 7,766,886 B2 | 8/2010 | Garcia et al. |
| 7,823,221 B2 | 11/2010 | Green |
| 7,942,856 B2 | 5/2011 | Lentini |
| 7,959,671 B2 | 6/2011 | Mangiardi et al. |
| 7,976,521 B2 | 7/2011 | Hara et al. |
| 8,012,194 B2 | 9/2011 | Edwin et al. |
| 8,066,657 B2 | 11/2011 | Frazer |
| 8,206,436 B2 | 6/2012 | Mangiardi et al. |
| 8,226,621 B2 | 7/2012 | Timmons |
| 8,235,939 B2 | 8/2012 | Johnson et al. |
| 8,262,719 B2 | 9/2012 | Erickson et al. |
| 8,292,860 B1 | 10/2012 | Persichetti et al. |
| 8,348,914 B2 | 1/2013 | Zyburt et al. |
| 8,357,193 B2 | 1/2013 | Phan et al. |
| 8,366,690 B2 | 2/2013 | Locke et al. |
| 8,414,635 B2 | 4/2013 | Hyodoh et al. |
| 8,425,539 B2 | 4/2013 | Binmoeller et al. |
| 8,439,934 B2 | 5/2013 | Satasiya et al. |
| 8,454,632 B2 | 6/2013 | Binmoeller et al. |
| 8,518,099 B2 | 8/2013 | Chanduszko et al. |
| 8,524,132 B2 | 9/2013 | Von Oepen et al. |
| 8,535,366 B2 | 9/2013 | Mangiardi et al. |
| 8,636,721 B2 | 1/2014 | Alam et al. |
| 8,641,692 B2 | 2/2014 | Tout et al. |
| 8,652,099 B2 | 2/2014 | Fierens et al. |
| 8,677,874 B2 | 3/2014 | Lilburn et al. |
| 8,696,611 B2 | 4/2014 | Yaacov et al. |
| 8,715,334 B2 | 5/2014 | Clerc et al. |
| 8,814,839 B2 | 8/2014 | Christensen et al. |
| 8,834,558 B2 | 9/2014 | Nissl |
| 8,906,081 B2 | 12/2014 | Cully et al. |
| 8,926,683 B2 | 1/2015 | Darla et al. |
| 8,961,448 B2 | 2/2015 | Forsell |
| 8,992,492 B2 | 3/2015 | Anderson et al. |
| 9,155,643 B2 | 10/2015 | Clerc et al. |
| 9,192,496 B2 | 11/2015 | Robinson |
| 9,259,336 B2 | 2/2016 | Schaeffer et al. |
| 9,284,637 B2 | 3/2016 | Boyle et al. |
| 9,381,041 B2 | 7/2016 | Brown et al. |
| 10,285,834 B2 | 5/2019 | Cindrich et al. |
| 2001/0037141 A1 | 11/2001 | Tee et al. |
| 2002/0068037 A1 | 6/2002 | Platzet et al. |

(56) References Cited

U.S. PATENT DOCUMENTS

| | | |
|---|---|---|
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0023268 A1 | 1/2003 | Lizardi |
| 2003/0028236 A1 | 2/2003 | Gillick |
| 2003/0050686 A1 | 3/2003 | Raeder-Devens et al. |
| 2003/0135265 A1 | 7/2003 | Stinson |
| 2003/0135268 A1 | 7/2003 | Desai |
| 2003/0144671 A1 | 7/2003 | Brooks et al. |
| 2003/0163101 A1 | 8/2003 | Say |
| 2003/0167060 A1 | 9/2003 | Buzzard et al. |
| 2004/0030381 A1 | 2/2004 | Shu |
| 2004/0098077 A1 | 5/2004 | Gianotti |
| 2004/0127973 A1 | 7/2004 | Mangiardi et al. |
| 2004/0181239 A1 | 9/2004 | Dorn et al. |
| 2004/0193243 A1 | 9/2004 | Mangiardi et al. |
| 2004/0267281 A1 | 12/2004 | Harari et al. |
| 2005/0004447 A1 | 1/2005 | Yamamoto |
| 2005/0027345 A1 | 2/2005 | Horan et al. |
| 2005/0038495 A1 | 2/2005 | Greenan |
| 2005/0090887 A1 | 4/2005 | Pryor |
| 2005/0125050 A1 | 6/2005 | Carter et al. |
| 2005/0149160 A1 | 7/2005 | McFerran |
| 2005/0182475 A1 | 8/2005 | Jen et al. |
| 2005/0278010 A1 | 12/2005 | Richardson |
| 2005/0283179 A1 | 12/2005 | Lentz |
| 2006/0020321 A1 | 1/2006 | Parker |
| 2006/0155368 A1 | 7/2006 | Shin |
| 2006/0184224 A1 | 8/2006 | Angel |
| 2006/0258972 A1 | 11/2006 | Mangiardi et al. |
| 2006/0259113 A1 | 11/2006 | Nissl |
| 2007/0002122 A1 | 1/2007 | Murano et al. |
| 2007/0005122 A1 | 1/2007 | Inoue |
| 2007/0043421 A1 | 2/2007 | Mangiardi et al. |
| 2007/0100421 A1 | 5/2007 | Griffin |
| 2007/0135904 A1 | 6/2007 | Eidenschink et al. |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0108948 A1 | 5/2008 | Beaver |
| 2008/0114443 A1 | 5/2008 | Mitchell et al. |
| 2008/0140178 A1 | 6/2008 | Rasmussen et al. |
| 2008/0177252 A1 | 7/2008 | Isik |
| 2008/0228256 A1 | 9/2008 | Erickson et al. |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0143731 A1 | 6/2009 | Guzman |
| 2009/0157158 A1 | 6/2009 | Ondracek |
| 2009/0171427 A1 | 7/2009 | Melsheimer et al. |
| 2009/0171433 A1 | 7/2009 | Melsheimer |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0030321 A1 | 2/2010 | Mach |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0070016 A1 | 3/2010 | Dorn |
| 2010/0145431 A1 | 6/2010 | Wu et al. |
| 2010/0174227 A1 | 7/2010 | Ramella et al. |
| 2010/0252470 A1 | 10/2010 | Ryan et al. |
| 2010/0274229 A1 | 10/2010 | Duocastella Codina et al. |
| 2011/0004290 A1 | 1/2011 | Bales, Jr. et al. |
| 2011/0015616 A1 | 1/2011 | Straubinger et al. |
| 2011/0082464 A1 | 4/2011 | Douk et al. |
| 2011/0137396 A1 | 6/2011 | Dorn et al. |
| 2011/0137400 A1 | 6/2011 | Dorn et al. |
| 2011/0190710 A1 | 8/2011 | Miyoshi |
| 2011/0190862 A1 | 8/2011 | Mehran et al. |
| 2011/0208296 A1 | 8/2011 | Duffy et al. |
| 2011/0230863 A1 | 9/2011 | Lentini |
| 2011/0264191 A1 | 10/2011 | Rothstein |
| 2011/0288482 A1 | 11/2011 | Farrell et al. |
| 2011/0307070 A1 | 12/2011 | Clerc et al. |
| 2011/0313360 A1 | 12/2011 | Lin |
| 2011/0319980 A1 | 12/2011 | Ryan |
| 2012/0046729 A1 | 2/2012 | Von Oepen et al. |
| 2012/0095567 A1 | 4/2012 | Weisman et al. |
| 2012/0136426 A1 | 5/2012 | Phan et al. |
| 2012/0197203 A1 | 8/2012 | Nokes, Jr. et al. |
| 2012/0283679 A1 | 11/2012 | Berish et al. |
| 2012/0290066 A1 | 11/2012 | Nabulsi et al. |
| 2012/0296257 A1 | 11/2012 | Van Dan et al. |
| 2012/0303109 A1 | 11/2012 | Okuma |
| 2012/0303112 A1 | 11/2012 | Armstrong et al. |
| 2012/0310320 A1 | 12/2012 | Gill et al. |
| 2013/0018215 A1 | 1/2013 | Snider et al. |
| 2013/0060205 A1 | 3/2013 | Mansour et al. |
| 2013/0103163 A1 | 4/2013 | Krimsky et al. |
| 2013/0110221 A1 | 5/2013 | Campbell et al. |
| 2013/0116770 A1 | 5/2013 | Robinson |
| 2013/0116771 A1 | 5/2013 | Robinson |
| 2013/0116772 A1 | 5/2013 | Robinson et al. |
| 2013/0158673 A1 | 6/2013 | Toomey |
| 2013/0184833 A1 | 7/2013 | Ryan et al. |
| 2013/0197623 A1 | 8/2013 | McHugo |
| 2013/0226114 A1 | 8/2013 | Massi et al. |
| 2013/0231689 A1 | 9/2013 | Binmoeller et al. |
| 2013/0245585 A1 | 9/2013 | Letellier |
| 2013/0253546 A1 | 9/2013 | Sander et al. |
| 2013/0274870 A1 | 10/2013 | Lombardi et al. |
| 2013/0296814 A1 | 11/2013 | Antholz |
| 2014/0031735 A1 | 1/2014 | Zurovick |
| 2014/0074065 A1 | 3/2014 | Muni et al. |
| 2014/0074219 A1 | 3/2014 | Hingston et al. |
| 2014/0155744 A1 | 6/2014 | Pameijer |
| 2014/0162400 A1 | 6/2014 | Vail et al. |
| 2014/0171863 A1 | 6/2014 | Blacker |
| 2014/0194778 A1 | 7/2014 | Uziel et al. |
| 2014/0196792 A1 | 7/2014 | Torres-Leon |
| 2014/0236064 A1 | 8/2014 | Binmoeller et al. |
| 2014/0243992 A1 | 8/2014 | Walsh et al. |
| 2014/0249412 A1 | 9/2014 | Yamamoto |
| 2014/0277573 A1 | 9/2014 | Gill et al. |
| 2014/0288636 A1 | 9/2014 | Headley, Jr. et al. |
| 2014/0303709 A1 | 10/2014 | Dwork |
| 2014/0330305 A1 | 11/2014 | Rood et al. |
| 2014/0350694 A1 | 11/2014 | Behan |
| 2014/0364959 A1 | 12/2014 | Attar et al. |
| 2015/0066128 A1 | 3/2015 | Losordo et al. |
| 2015/0100133 A1 | 4/2015 | Xie et al. |
| 2015/0112377 A1 | 4/2015 | Arnone et al. |
| 2015/0173919 A1 | 6/2015 | Baldwin |
| 2015/0230955 A1 | 8/2015 | Farag Eells et al. |
| 2015/0297880 A1 | 10/2015 | Ogawa et al. |
| 2015/0313595 A1 | 11/2015 | Houshton et al. |
| 2015/0313599 A1 | 11/2015 | Johnson et al. |
| 2016/0032769 A1 | 2/2016 | Stutz et al. |
| 2016/0081823 A1 | 3/2016 | Majercak |
| 2016/0081832 A1 | 3/2016 | Hingston et al. |
| 2016/0242846 A1 | 8/2016 | Brown et al. |
| 2016/0256306 A1 | 9/2016 | Cindrich et al. |
| 2017/0014133 A1 | 1/2017 | Han et al. |
| 2017/0035424 A1 | 2/2017 | Binmoeller et al. |
| 2017/0035426 A1 | 2/2017 | Phan et al. |
| 2017/0035427 A1 | 2/2017 | Sander et al. |
| 2017/0035428 A1 | 2/2017 | Binmoeller et al. |
| 2017/0354404 A1 | 12/2017 | Chu |
| 2018/0185183 A1 | 7/2018 | Christakis et al. |
| 2018/0263797 A1 | 9/2018 | Eller et al. |
| 2018/0303594 A1 | 10/2018 | Eller et al. |
| 2019/0099589 A1 | 4/2019 | Walsh et al. |
| 2021/0161692 A1 | 6/2021 | Mower et al. |
| 2022/0023026 A1 | 1/2022 | Eller et al. |

(56) References Cited

U.S. PATENT DOCUMENTS

| | | | |
|---|---|---|---|
| 2022/0125608 | A1 | 4/2022 | Ethridge et al. |
| 2022/0211527 | A1 | 7/2022 | Mower et al. |

FOREIGN PATENT DOCUMENTS

| | | |
|---|---|---|
| DE | 4323866 | 1/1994 |
| DE | 102005051469 | 4/2007 |
| EP | 0364420 | 4/1990 |
| EP | 0408245 | 1/1991 |
| EP | 0872220 | 10/1998 |
| EP | 1637092 | 3/2006 |
| EP | 2522316 | 11/2012 |
| GB | 2243786 | 9/1989 |
| WO | 199631174 | 10/1996 |
| WO | 200018330 | 4/2000 |
| WO | 2000078246 | 12/2000 |
| WO | 2002056798 | 7/2002 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2012062603 A1 | 5/2012 |
| WO | 2012062603 | 10/2012 |
| WO | 2013045262 | 4/2013 |
| WO | 2013052528 | 4/2013 |
| WO | 2013066883 | 10/2013 |
| WO | 2015184154 | 12/2015 |
| WO | 2019099080 | 5/2019 |
| WO | 2020146261 | 7/2020 |

OTHER PUBLICATIONS

European Search Report dated Mar. 19, 2021 for EP18768455.0.
Office Action dated May 21, 2021 for U.S. Appl. No. 15/921,220.
European Search Report dated Nov. 9, 2020 for EP18767753.9.
European Search Report dated Dec. 15, 2020 for EP18768455.0.
Office Action dated Dec. 22, 2020 for U.S. Appl. No. 15/921,220.
European Examination Report dated Feb. 18, 2015 for EP09791142.4.
European Search Report dated Apr. 24, 2020 for EP17857414.1.
European Search dated Sep. 24, 2018 for EP 16759580.
International Preliminary Report dated May 15, 2014 for PCT/US2012/062603.
International Publication and Search Report dated Jun. 14, 2012 for WO2012078794.
International Publication and Search Report dated Feb. 25, 2012 for WO2010021836.
International Publication and Search Report dated Aug. 4, 2005 for WO2005070095.
International Search Report and Written Opinion dated Jan. 9, 2018 for PCT/US2017/054000.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated Jun. 22, 2016 for PCT/US2016/020900.
International Search Report and Written Opinion dated Jun. 29, 2018 for PCT/US2018/022340.
International Search Report and Written Opinion dated Jun. 29, 2018 for PCT/US2018/022344.
International Search Report and Written Opinion dated Aug. 2, 2018 for PCT/US2018/028107.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Feb. 25, 2019 for U.S. Appl. No. 15/061,107.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Sep. 11, 2019 for U.S. Appl. No. 15/263,741.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
Office Action dated Jan. 22, 2013 for U.S. Appl. No. 10/585,430.
Office Action dated Jan. 31, 2012 for U.S. Appl. No. 10/585,430.
Office Action dated Feb. 5, 2020 for U.S. Appl. No. 15/921,172.
Office Action dated Mar. 6, 2020 for U.S. Appl. No. 15/955,895.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 7, 2020 for U.S. Appl. No. 15/955,895.
Office Action dated Apr. 25, 2018 for U.S. Appl. No. 15/061,107.
Office Action dated May 5, 2014 for U.S. Appl. No. 13/313,929.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2015 for U.S. Appl. No. 13/664,267.
Office Action dated Oct. 16, 2017 for U.S. Appl. No. 15/061,107.
Office Action dated Nov. 9, 2010 for U.S. Appl. No. 10/585,430.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 30, 2016 for U.S. Appl. No. 13/664,137.
Office Action dated Dec. 7, 2009 for U.S. Appl. No. 11/432,964.
Office Action dated Dec. 8, 2009 for U.S. Appl. No. 10/585,430.
Cheon, et al., Clinical Feasibility of a New Through-the-Scope Fully Covered Esophageal Self-Expandable Metallic Stent: an in Vivo Animal Study, Digestive Endoscopy, vol. 26 No. 1, 2014, 32-36.
Kawakami, et al., Endoscopic Ultrasound-Guided Transluminal Drainage for Peripancreatic Fluid Collections: Where are we now?, Gut and Liver, vol. 8 No. 4, 2014, 341-355.
Sen, et al., Laplace's Equation for Convective Scalar Transport in Potential Flow, Proc. R. Soc. Lond. A 456, pp. 3041-3045, 2000.
Sizarov, et al., Novel materials and Devices in the Transcatheter Creation of vascular Anastomosis—The Future Domes Slowly (Part 2), Archives of Cardiovascular Diseases, vol. 109 No. 4, 2016, 286-295.
Weilert, et al., Specially Designed Stents forTranslumenal Drainage, Gastrointestinal Intervention, vol. 4 No. 1, 2015, 40-45.
European Examination Report dated Feb. 2, 2023 for EP 18768455.0.
Notice of Allowance dated Jan. 5, 2023 for U.S. Appl. No. 15/921,220.
European Search Report dated Feb. 3, 2015 for EP12846255.3.
European Search Report dated Apr. 9, 2018 for EP15860892.7.
European Search Report dated May 4, 2007 for EP05705271.4.
European Search Report dated Jun. 30, 2017 for EP11846358.7.
International Publication and Search Report dated Dec. 19, 2006 for WO2005070095.

(56) References Cited

OTHER PUBLICATIONS

Office Action dated Dec. 2, 2019 for U.S. Appl. No. 15/718,419.
International Search Report and Written Opinion dated Feb. 14, 2022 for PCT/US2021/056495.
International Search Report and Written Opinion dated May 10, 2013 for PCT/US2012/060364.
International Search Report and Written Opinion dated Sep. 12, 2016 for PCT/US2016/040174.
International Search Report and Written Opinion dated Nov. 9, 2021 for PCT/US2021/042833.
Notice of Allowance dated Jul. 22, 2020 for U.S. Appl. No. 15/718,419.
Office Action dated Apr. 15, 2022 for U.S. Appl. No. 15/921,220.
Office Action dated Apr. 23, 2020 for U.S. Appl. No. 15/596,823.
Office Action dated Jun. 23, 2020 for U.S. Appl. No. 15/696,440.
Office Action dated Oct. 16, 2019 for U.S. Appl. No. 15/596,823.
Office Action dated Nov. 9, 2021 for U.S. Appl. No. 15/921,221.

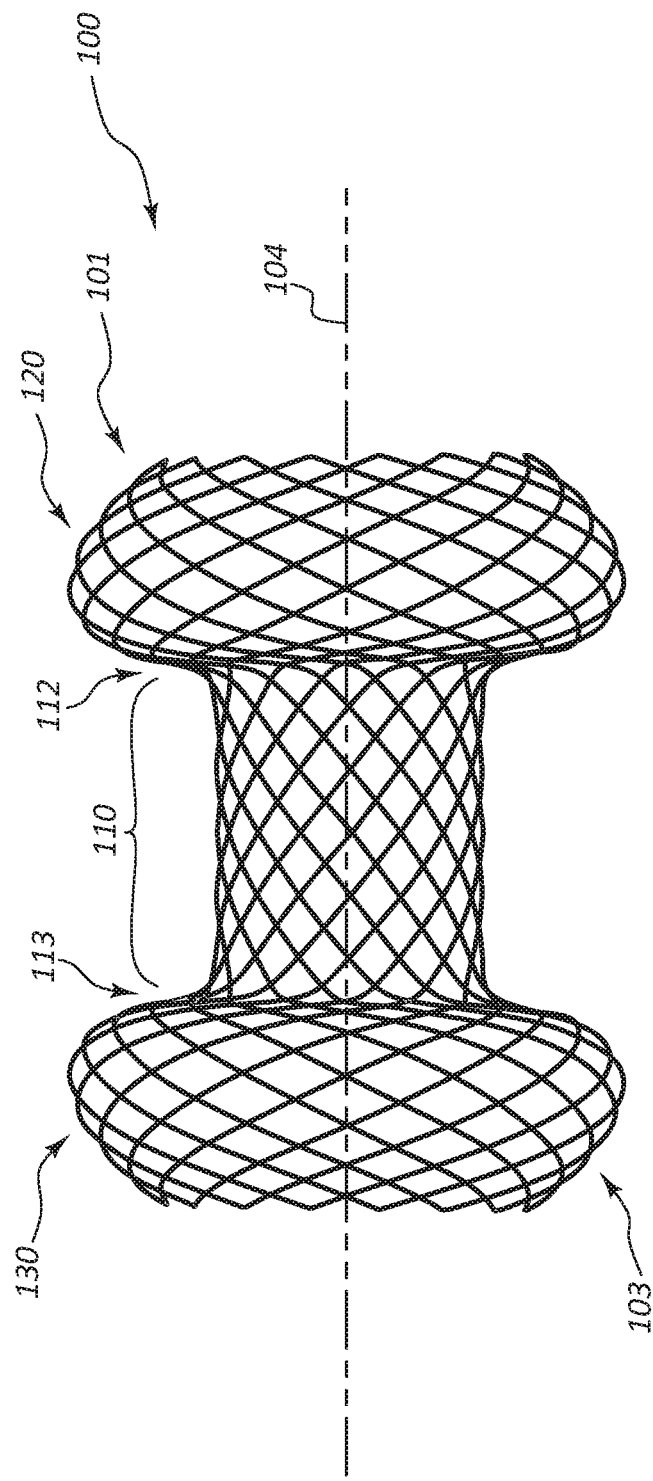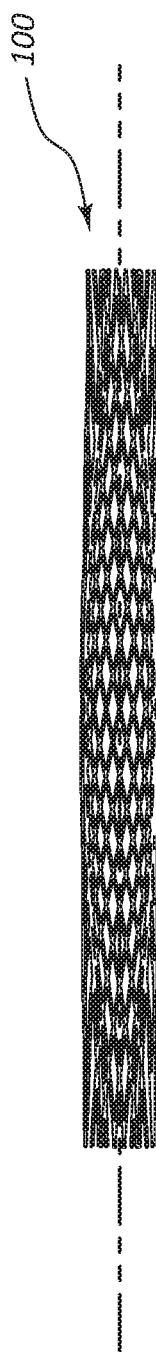
FIG. 1
FIG. 2

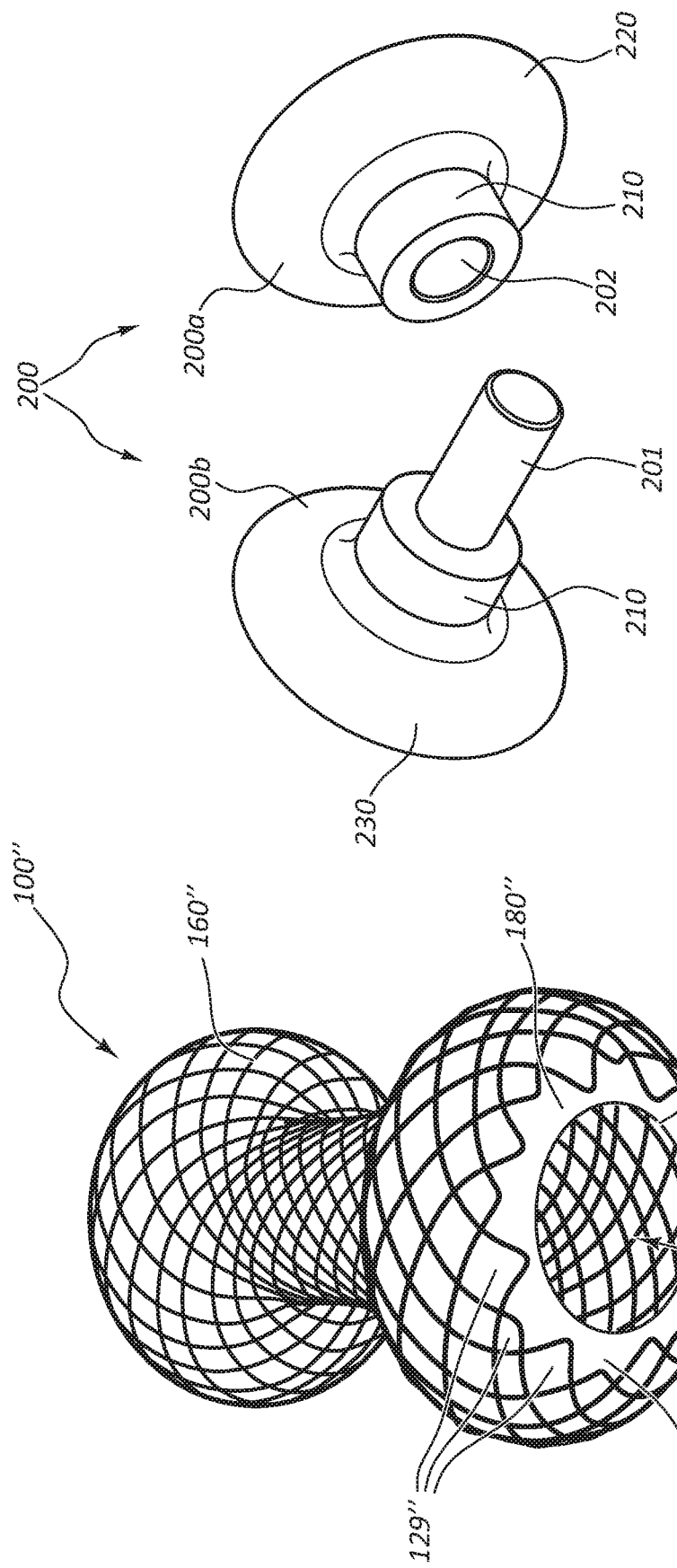

STENTS AND RELATED METHODS

RELATED APPLICATIONS

This application is a continuation of U.S. patent application Ser. No. 15/921,172 filed Mar. 14, 2018, and titled "Transluminal Stents and Related Methods," which claims priority to U.S. Provisional Application No. 62/471,746 filed Mar. 15, 2017, and titled "Transluminal Stents and Related Methods," each of which is hereby incorporated by reference in its entirety.

TECHNICAL FIELD

This application generally relates to medical devices. More particularly, this application relates to stents and related methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 illustrates an exemplary embodiment of a stent in an unelongated and unstretched state, such as when in use in vivo.

FIG. 2 illustrates the exemplary embodiment of FIG. 1 in an elongated and stretched state, such as when loaded in a stent pod of a delivery catheter prior to deployment in vivo.

FIG. 7 illustrates an exemplary embodiment similar to the embodiment of FIG. 1, but with staggered end loops.

FIG. 8 illustrates an exemplary embodiment of a mandrel for use in manufacturing the exemplary embodiment of FIG. 1.

DETAILED DESCRIPTION

Figure 3:
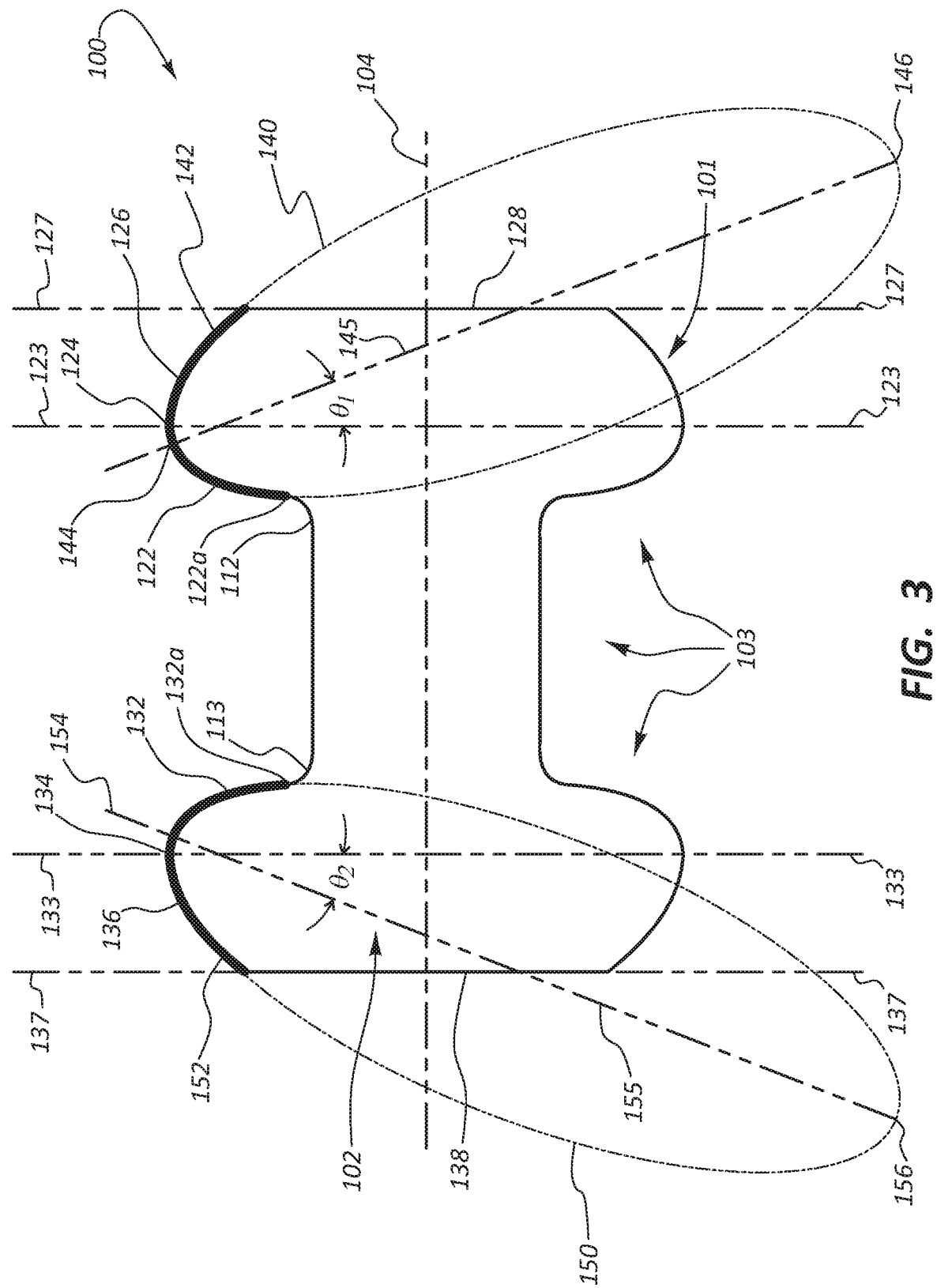
FIG. 3 illustrates the shape of the exemplary embodiment of FIG. 1.

Stents are disclosed herein. In some embodiments, the stents described herein comprise a hollow cylindrical body having an interior dimension and an exterior dimension and comprising a middle region that extends to a first flared end and also extends to an opposing second flared end. The interior dimension refers to the three dimensional space within the stent, while the exterior dimension refers to the space outside of the stent. As used herein, the hollow cylindrical body may refer to generally cylindrical shapes and forms, including stents with flared ends, for example.

The first flared end may comprise a first inner shoulder, a first crest, a first outer taper, and a first opening. The first inner shoulder may extend from one end of the middle region to the first crest. A diameter of the first crest may be greater than a diameter of the middle region. The first outer shoulder may extend from the first crest to the first opening. The first opening may provide a first boundary between the interior dimension and the exterior dimension.

Likewise, the second flared end may comprise a second inner shoulder, a second crest, a second outer taper, and a second opening. The second inner shoulder may extend from one end of the middle region to the second crest. The diameter of the second crest may be greater than a diameter of the middle region. The second outer shoulder may extend from the second crest to the second opening. The second opening may provide a second boundary between the interior dimension and the exterior dimension.

In some embodiments, the hollow cylindrical body may be characterized by a longitudinal plane that bisects the hollow cylindrical body along its longitudinal axis, may be characterized by a first perpendicular plane that encompasses a circle defined by the first crest, and may be characterized by a second perpendicular plane that encompasses a circle defined by the second crest, where the first and second perpendicular planes are perpendicular to the longitudinal plane. In such embodiments, a profile of at least a portion of the first inner shoulder, the first crest, and at least a portion of the first outer taper may circumscribe a portion of a first elliptical arc of a first ellipse that lies in the longitudinal plane. The first elliptical arc may include an upper antipodal point of the first ellipse and a lower antipodal point of the first ellipse may be outwardly offset along the longitudinal plane relative to the first perpendicular plane and the middle region. Likewise, in such embodiments, a profile of at least a portion of the second inner shoulder, the second crest, and at least a portion of the second outer taper may circumscribe a portion of a second elliptical arc of a second ellipse that lies in the longitudinal plane. The second elliptical arc may include an upper antipodal point of the second ellipse and a lower antipodal point of the second ellipse may be outwardly offset along the longitudinal plane relative to the second perpendicular plane and the middle region.

In some embodiments, the hollow cylindrical body may comprise braided or woven wires having a constant pitch along a length of the middle region. The braided or woven wires may have a uniformly varying pitch along the first inner shoulder. The braided or woven wires may have a constant pitch at the first crest. The braided or woven wires may have a uniformly varying pitch along the first outer taper. The braided or woven wires may have a uniformly varying pitch along the second inner shoulder. The braided or woven wires may have a constant pitch at the second crest. The braided or woven wires may have a uniformly varying pitch along the second outer taper.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "communication with" and "coupled to" are used in their ordinary sense, and are broad enough to refer to any suitable coupling or other form of interaction between two or more entities, including mechanical, electrical, magnetic, electromagnetic, fluid, and thermal interaction. Two components may interact with each other even though they are not in direct contact with each other. For example, two components may be coupled to each other through an intermediate component. The directional terms "proximal" and "distal" are used herein to refer to opposite locations on a component or device. The proximal end of a component or device is defined as the end of the device closest to the practitioner when the device is in normal use by the practitioner. The distal end is the end opposite the proximal end, along the longitudinal direction of the device, or the end farthest from the practitioner during normal use.

FIG. 1 illustrates an exemplary embodiment of a stent 100 in an unelongated and unstretched state, such as when in use in vivo. Stent 100 comprises a hollow cylindrical body 101 having an interior dimension 102 (see FIG. 3) and an exterior dimension 103. The hollow cylindrical body 101 comprises a middle region 110 that extends to a first flared end 120 and also extends to an opposing second flared end 130.

In some embodiments, the overall length of the stent 100 in the unelongated and unstretched state may range from 15 to 36 mm, including ranging from 20 to 34 mm or from 24 to 28 mm. In some embodiments, the length of the first flared end 120 and/or the second flared end 130 in the unelongated and unstretched state may each range from 3.5 to 8 mm, including ranging from 6 to 8 mm. In some embodiments, the length of the middle region 110 in the unelongated and unstretched state may range from 8 to 20 mm, including ranging from 10 to 16 mm.

FIG. 2 illustrates the exemplary embodiment of FIG. 1 in an elongated and stretched state, such as when loaded in a stent pod of a delivery catheter prior to deployment in vivo.

In some embodiments, the overall length of the stent 100 in the elongated and stretched state may range from 40 to 74 mm, including ranging from 46 to 72 mm or from 60 to 70 mm. In some embodiments, the length of the first flared end 120 and/or the second flared end 130 in the elongated and stretched state may each range from 15 to 23 mm, including ranging from 16 to 21 mm. In some embodiments, the length of the middle region 110 in the elongated and stretched state may range from 15 to 23 mm, including ranging from 16 to 21 mm.

FIG. 3 illustrates the shape of the exemplary embodiment of FIG. 1. The first flared end comprises a first inner shoulder 122, a first crest 124, a first outer taper 126, and a first opening 128. The first inner shoulder 122 extends from a proximal end 112 of the middle region 110 to the first crest 124. In the illustrated embodiment, the diameter of the first crest 124 is greater than the diameter of the middle region 110, for example, about 1.3 to about 2.9 times, such as about 1.4 to about 2.9 and such as about 1.3 to about 2.0, the diameter of the middle region 110. The first outer taper 126 extends from the first crest 124 to the first opening 128. The first opening 128 provides a first boundary between the interior dimension 102 and the exterior dimension 103.

Likewise, the second flared end 130 comprises a second inner shoulder 132, a second crest 134, a second outer taper 136, and a second opening 138. The second inner shoulder 132 extends from the distal end 113 of the middle region 110 to the second crest 134. The diameter of the second crest 134 is greater than the diameter of the middle region 110, for example, about 1.6 to about 2.5 times the diameter of the middle region 110. The second outer taper 136 extends from the second crest 134 to the second opening 138. The second opening 138 provides a second boundary between the interior dimension 102 and the exterior dimension 103. In the illustrated embodiments, the diameter of the first opening 128 is greater than the diameter of the middle region 110, but less than the diameter of the first crest 124. Likewise, the diameter of the second opening 138 is greater than the diameter of the middle region 110, but less than the diameter of the second crest 134. This can facilitate removal of the stent 100 from a mandrel 200, as will be discussed more below in relation to FIG. 8.

This can also reduce particle entrapment during drainage via the interior dimension 102. Particles and fluid can tend to fill the interior dimension 102 of the first and second flared ends 120 and 130 during use, such as drainage of the gall bladder, a biliary tract, or a pancreatic cyst. When the diameter of the first and second openings 128 and 138 are the same diameter or smaller than the diameter of the middle region 110, this can make removal of fluid and particles from the interior dimension 102 of the first and second flared ends 120 and 130 difficult. Increasing the diameter of the first and second openings 128 and 138, relative to the diameter of the middle region 110, can facilitate particle and fluid removal from the interior dimension 102 of the first and second flared ends 120 and 130.

In an alternative embodiment, the first crest 124 may form a planar region (cylindrical region from a perspective view) parallel to the middle region 110. In this alternative embodiment, the diameter of the first crest 124 could still be greater than the diameter of the middle region 110. Likewise, the second crest 134 may form a planar region parallel to the middle region 110.

In addition, the first opening 128 may comprise a cylindrical region that proximally extends the longitudinal length of the stent 100. The first opening 128 would terminate at the proximal end of the cylindrical region. The cylindrical region would be coaxial with the longitudinal axis 104. The planar surface of the cylindrical region (from a profile view) would be parallel to the middle region 110. Likewise, the second opening 138 may comprise a cylindrical region that distally extends the longitudinal length of the stent 100. The second opening 138 would terminate at the distal end of the cylindrical region.

FIG. 3 illustrates the hollow cylindrical body 101 bisected in a longitudinal plane along its longitudinal axis 104. The hollow cylindrical body 101 is characterized by a first perpendicular plane 123 that encompasses a circle defined by the first crest 124 and characterized by a second perpendicular plane 133 that encompasses a circle defined by the second crest 134. The first and second perpendicular planes 123 and 133 are perpendicular to the longitudinal plane (i.e., the page). In the illustrated embodiment, a profile of at least a portion of the first inner shoulder 122, the first crest 124, and at least a portion of the first outer taper 126 circumscribe a first elliptical arc 142 of a first ellipse 140 that lies in the longitudinal plane. The first elliptical arc 142 includes an upper antipodal point 144 and a lower antipodal point 146. The upper antipodal point 144 is inwardly inset relative to the first perpendicular plane 123 (and the middle region 110) and the lower antipodal point 146 is outwardly offset relative to the first perpendicular plane 123. Likewise, in such embodiments, a profile of at least a portion of the second inner shoulder 132, the second crest 134, and at least a portion of the second outer taper circumscribes a second elliptical arc 152 of a second ellipse 150 that lies in the longitudinal plane (i.e., the page). The second elliptical arc 152 includes an upper antipodal point 154 and a lower antipodal point 156 of the second ellipse. The upper antipodal point 154 is inwardly inset relative to the second perpendicular plane 133 (and the middle region 110) and the lower antipodal point 156 is outwardly offset relative to the second perpendicular plane 133.

For example, the lower antipodal point 146 may be outwardly offset along the longitudinal plane 104 relative to the first perpendicular plane 123 and the major axis 145 of the first ellipse 140 by an angle $\theta_1$ of about 5 degrees to about 60 degrees, about 10 degrees to about 45 degrees, about 10 degrees to about 40 degrees, or about 10 degrees to about 25 degrees. Likewise, for example, the lower antipodal point 156 may be outwardly offset along the longitudinal plane 104 relative to the second perpendicular plane 133 and the major axis 145 by an angle $\theta_2$ of about −5 degrees to about −60 degrees, about −10 degrees to about −45 degrees, about −10 degrees to about −40 degrees, or about −10 degrees to about −25 degrees.

In the illustrated embodiments, the profile of the second flared end 130 is a mirror image of the first flared end 120. In alternative embodiments, the shape of the second flared end 120 may differ from the shape of the first flared end 110, in some cases, significantly.

Figure 4:
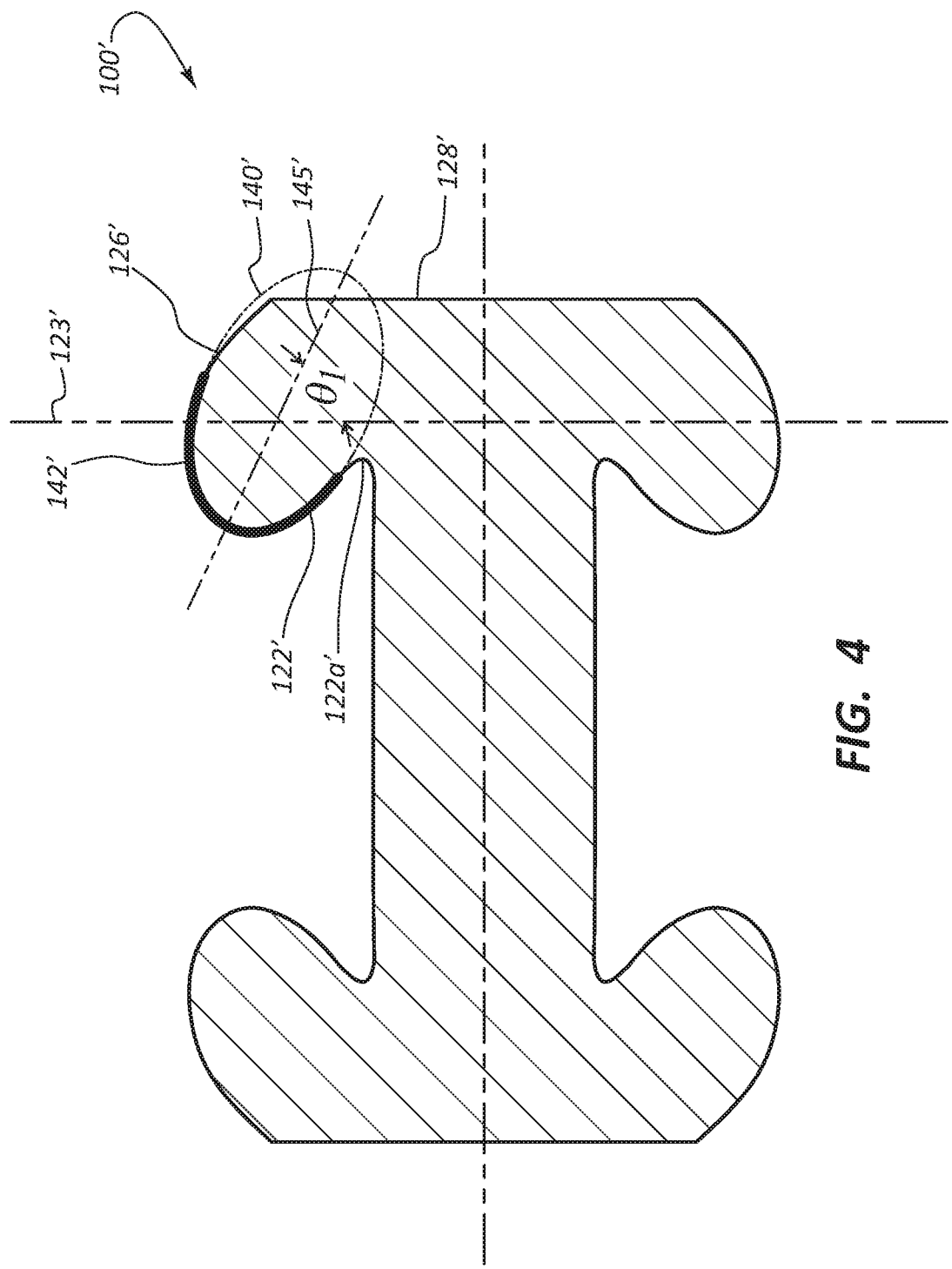
FIG. 4 illustrates the shape of an additional exemplary embodiment.

FIG. 4 illustrates an exemplary embodiment of stent 100' where $\theta_1$ (as defined by the first perpendicular plane 123' and the major axis of the first ellipse 145') and $\theta_2$ ($\theta_2$ not shown) are about 45 degrees and −45 degrees, respectively. It should be understood that the disclosure regarding the stent 100 applies equally to the stent 100', other than as specifically delineated. In FIG. 4, the first elliptical arc 142' of the first ellipse 140' circumscribes a portion of the first shoulder 122', but does not extend to the first perpendicular region 122a'. Likewise, the first elliptical arc 142' circumscribes a portion of the first outer taper 126', but does not extend to the first opening 128'.

In the illustrated embodiments, the first inner shoulder 122 comprises a first perpendicular region 122a concentrically surrounding and perpendicular to the middle region 110. The first elliptical arc 142 extends from the first perpendicular region 122a, along the first crest 124, and along the first outer taper 126 to the first opening 128. Likewise, the second inner shoulder 132 comprises a second perpendicular region 132a concentrically surrounding and perpendicular to the middle region 110. The second elliptical arc 152 extends from the second perpendicular region 132a, along the second crest 134, and along the second outer taper 136 to the second opening 138. The first and second perpendicular regions 122a and 132a facilitate retention of the first and second inner shoulders 122 and 132 against tissue walls when the stent 100 is in use, as compared to flared ends 120 and 130 that do not include surfaces perpendicular to the middle region 110 in the inner shoulders 122 and 132.

In contrast, in the illustrated embodiments, the first and second outer tapers 126 and 136 do not include regions perpendicular to the middle region 110. This increases stiffness of the first and second flared ends 120 and 130, relative to a flared end that includes a perpendicular region in an outer shoulder. For example, a flared end that includes a symmetrical inner shoulder and outer shoulder (i.e., mirror image profiles), where both the inner shoulder and the outer shoulder include perpendicular regions, can tend to deflect more outwardly (relative to the middle region) when in use, as compared to embodiments such as the illustrated embodiments where the inner shoulders 122 and 132 include perpendicular regions 122a and 132a, but the outer tapers 126 and 136 do not include corresponding perpendicular regions. In alternative embodiments, one or both of the first and second outer tapers 126 and 136 may include regions perpendicular to the middle region 110.

Figure 5:
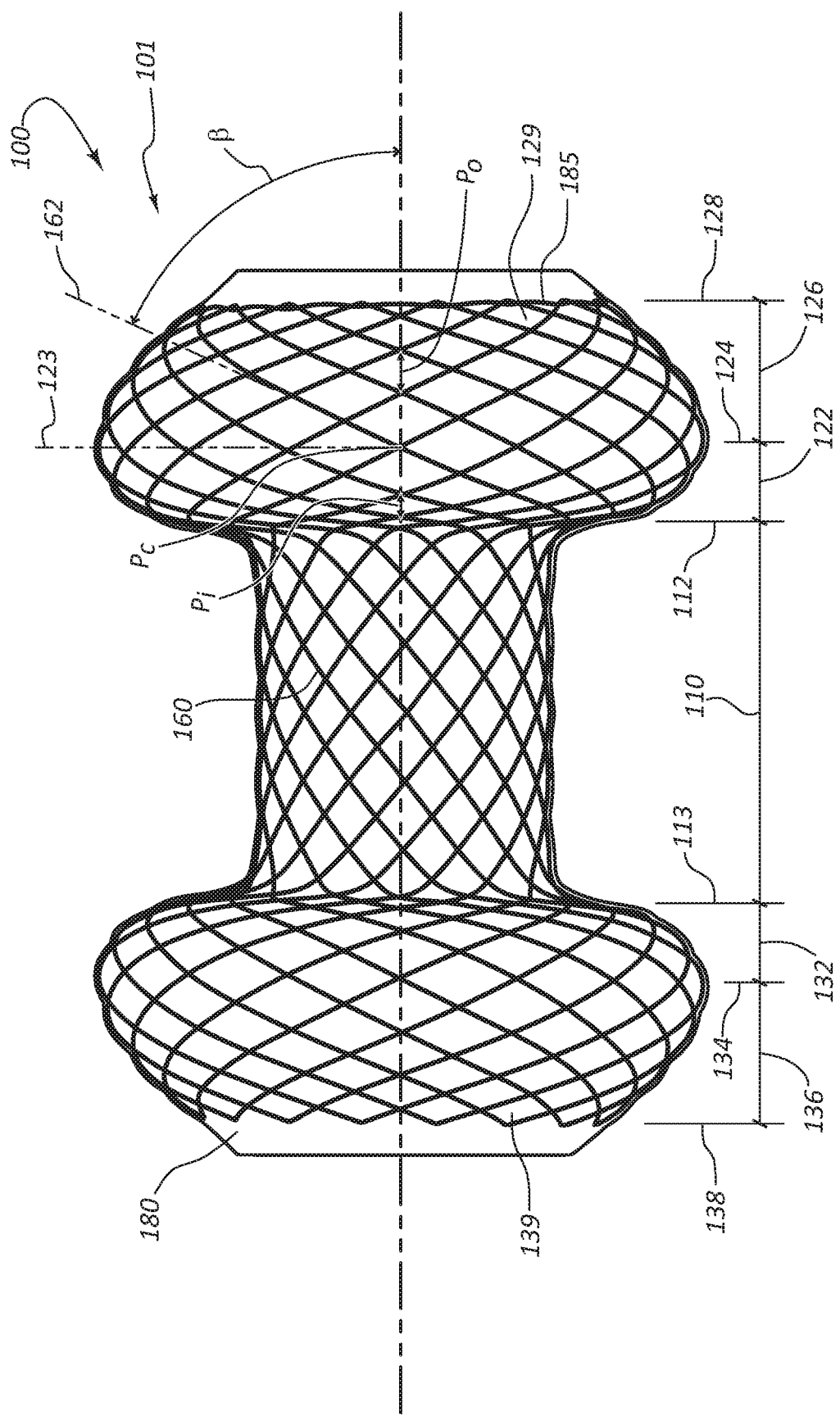
FIG. 5 illustrates braid angles and wire pitches for the exemplary embodiment of FIG. 1.
Figure 5A:
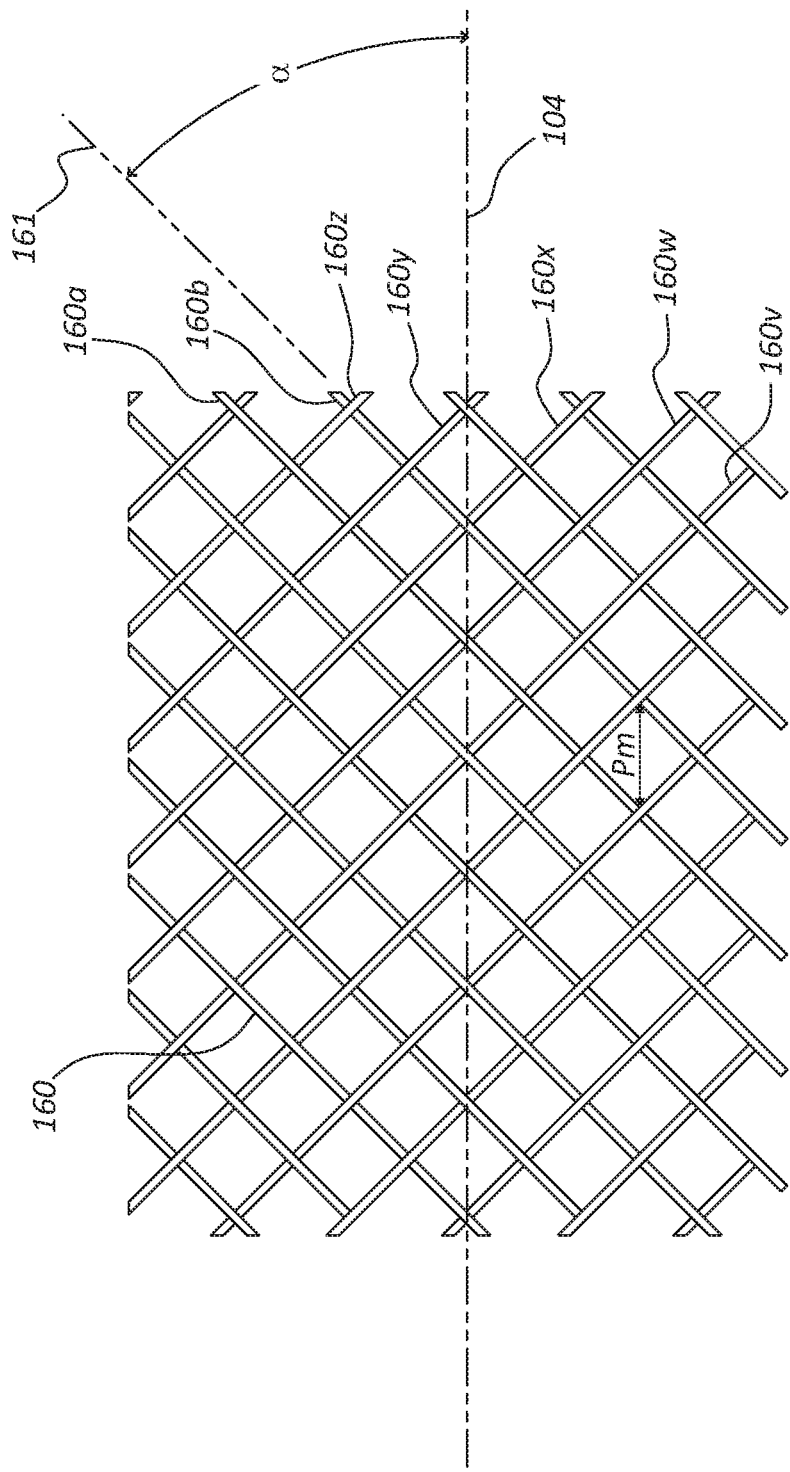
FIG. 5A is a close-up view of the braid pattern of the middle region of the exemplary embodiment of FIG. 1.

Turning now to FIG. 5, the hollow cylindrical body 101 may comprise braided or woven wires 160. FIG. 5A is a close-up view of a planarized version of the middle region 110 of the stent 100. This close-up view illustrates the braid pattern, the pitch, and the braid angle $\alpha$ of the middle region 110. The braid pattern of the middle region 110 (and of the entire stent 100) is a one-wire, two-over, two-under braid pattern (referred to as a "one over two" pattern), which means that a single strand passes over two strands (or two different portions of itself, such as in a single wire braid design) and then under two other strands (or yet two other portions of itself, such as in a single wire braid design). Specifically, a first strand 160a (or a first length 160a of a single strand) passes over a first intersecting strand 160v (or a first intersecting length 160v of a single strand), then passes over a second intersecting strand 160w (or a second intersecting length 160w of a single strand), passes under a third intersecting strand 160x (or a third intersecting length 160x of a single strand), and then passes under a fourth intersecting strand 160y (or a fourth intersecting length 160y of a single strand). The first strand 160a then repeats the pattern with additional strands. An adjacent second strand 160b (or a second length 160b of a single strand) offsets the pattern. Starting with the second intersecting strand 160w, the second strand 160b passes over the second intersecting strand 160w, passes over the third intersecting strand 160x, passes under the fourth intersecting strand 160y, and then passes under a fifth intersecting strand 160z. The one over two pattern may allow for easier elongation of the stent 100. For example, during elongation of the stent 100, a one over two pattern may facilitate change in the angle of intersection of the wires may as adjacent wires tend to align more with each other during elongation of the stent 100 (causing the intersecting wires to come together like scissors closing), which in turn may allow for use with a low-profile delivery catheter.

Alternative braid patterns may be used as well, such as a one-wire, one-over, one-under braid pattern (referred to as a "one over one" pattern). This braid pattern tends to facilitate stent removal from mandrels. Other possible braid patterns include the diamond two-wire, one-over, one-under braid pattern and the diamond two, two-over, two-under braid pattern.

In some embodiments, the braid pattern may lead to differing cell requirements over the length of the stent 100. A cell refers to the design created by the braid pattern. For example, FIG. 5 illustrates a diamond cell, however, alternative cell designs may be used in the stent 100. Thus, depending on stent length and braid pattern, the braid designs may result in fractional and non-fractional cell counts. In other words, a stent may be designed such that a full braid pattern is completed on each end of the stent and/or the stent comprises only full braid patterns along the length of the sent. Non-fractional cell counts refer to a whole cell count. For example a stent may have, 20, 30, 40, 50, or more full cell counts, or full braid patterns along its length. Fractional cell counts refer to fractional cell count numbers, 20.5, 30.5, 40.5, 50.5 or more, meaning the stent has a whole number of full cell counts in addition to a partial cell (or braid pattern) along the length of the stent. In some embodiments, the braid pattern may be one over one and may have a fractional or non-fractional cell count. In some embodiments, the braid pattern may be one over two and may have a fractional or non-fractional cell count.

The braid angle $\alpha$ is an angle formed by a given strand of the braided or woven wires 160, such as the second strand 160b, relative to the longitudinal axis 104 of the stent 100, when viewed as illustrated in FIG. 5A. A larger (higher) braid angle, approaching, for example, 90 degrees, results in a higher pick count (number of points of intersection of the strands 160) per given longitudinal length (e.g., an inch) of a given braid (or weaving) pattern. The higher pick count can produce greater stiffness (i.e., a lower degree of compressibility). A smaller (lower) braid angle results in a lower pick count per given longitudinal length, which can result in greater softness (i.e., less stiffness and a higher degree of compressibility). For example, in the illustrated embodiments, the braid angle α for the middle region 110 is about 45 degrees.

The pitch (i.e., lengthwise distance between intersecting strands) also impacts the compressibility and stiffness of the braided or woven wires 160. The pitch of the middle region 110 (Pm) is illustrated in FIG. 5A between first and second strands 160a and 160b. The Pm is governed by the number of strands interwoven (or interbraided) with each other and the braid angle α. For example, the Pm may be about 0.75 mm to about 2.25 mm for middle region 110 diameters of about 6 mm to about 26 mm. The Pm may be constant, as in the illustrated embodiments. The length of the middle region 110 may be any length, such as, for example, about 5 mm to about 3 cm.

Referring again to FIG. 5, the braided or woven wires 160 have a uniformly varying pitch along the first inner shoulder 122 (Pi), have a uniform pitch at the first crest 124 (Pc), and have a uniformly varying pitch along the first outer taper 126 (Po). Likewise, in the illustrated embodiment, the braided or woven wires 160 have a correspondingly uniform varying pitch along the second inner shoulder 132, have a correspondingly uniform pitch at the second crest 134, and a correspondingly uniform varying pitch along the second outer taper 136.

In the illustrated embodiments, Pc is less than Pm. In some embodiments, for smaller diameter stents, such as 6 mm and 8 mm stents, the Pc may be greater than Pm. Likewise, in some embodiments, for larger diameter stents, such as 10 mm, 15 mm, and 20 mm stents, the Pc may be less than Pm. For example, the Pc may be about 1.4 mm to about 2.0 mm, such as about 1.6 mm to about 1.8 mm, which may be more or less than the Pm.

Additionally, in the illustrated embodiments, Pi is continuously decreasing from the middle region 110 to the first crest 124. In contrast, Po is continuously increasing from the first crest 124 to the first opening 128. It should be understood that the uniform pitch of Pc refers to an instantaneous pitch at the first crest 124 governed by the braid angle β. The instantaneous pitch of Pc does not mean that the braided or woven wires 160 need to intersect at the first crest 124. Additionally, in the illustrated embodiments, the pitch is increasing distal to the first crest 124 (the first inner shoulder 122) and increasing proximal to the first crest 124 (the first outer taper 126). Therefore, there is not a constant pitch as there is for the middle region 110. However, the instantaneous pitch dictates the theoretical pitch of intersecting strands if they were laid out in a constant planar fashion, as in FIG. 5A, but utilizing the braid angle β and spacing dictated by the diameter of the first crest 124 and the number of braided or woven wires 160 utilized. It is the instantaneous pitch for Pc that is uniform as the braided or woven wires 160 cross the first crest 124.

Or stated another way, the braid angle continuously increases from the proximal end 112 of the middle region 110 to the first crest 124, and even though the diameter of the stent 100 is increasing as well, the pitch is continuously decreasing. The instantaneous braid angle β is uniform for all braided or woven wires 160 around the circumference of the first crest 124. The braid angle decreases from the first crest 124 to the first opening 128, and even though the diameter of the stent 100 is decreasing, the pitch continuously increases.

In the illustrated embodiment, the pitch of the braided or woven wires 160 at the first opening 128 is greater than the constant pitch Pm of the middle region 110. This may facilitate release from the mandrel 200 during manufacture. However, it may be desirable to have the Po at the opening 128 (i.e., the braid angle) be as small as possible, while still allowing for release from the mandrel. For example, the Po may be configured to allow the braided or woven wires 160 at the first opening 128 to expand almost equal to the diameter of the first crest 124. It should be understood that the discussion regarding pitch and braid angles for the first flared end 120 may apply equally to the second flared end 130.

As discussed above, in some embodiments, Pc may be equal to or greater than Pm. In such embodiments, the pitch of Pi may be continuously increasing or stay constant. In such embodiments, the pitch of Po may be decreasing, stay constant, or be increasing.

In some embodiments, the various pitches allow the stent 100 to be elongated and loaded into a 10.8 French or smaller catheter. It should be understood that the description regarding braid angle and pitches for the first flared end 120 applies equally to the second flared end 130.

FIG. 5 illustrates a suture line 185 woven through the first end loops 129. The suture line 185 may aid with loading of the stent 100 into a catheter and also aid with removal from a patient. The suture line 185 may be woven in such a way that pulling it has a "purse string" effect on the first opening 128. Additionally or alternatively, a suture line may be woven through the second end loops 139. The suture line 185 may be configured to be permanent or to be removable after the stent 100 is in place in a patient. The suture line 185 may be woven in place after a cover 180 (discussed in more detail below) has encapsulated the braided or woven wires 160, thereby allowing free movement of the suture line 185. The ends of the suture line 185 may be secured by a variety of ways, depending on the material of the suture line 185. For example, when the suture line 185 is made of a fiber, such as Teleflex Force Fiber, then the ends of the suture line 185 may be secured via a knot, adhesives, or a combination thereof. In another example, when the suture line 185 comprises a metal cable, then the ends may be secured via crimping, a metal band, or combinations thereof.

The braided or woven wires 160 may be braided or woven in a given pattern in accordance with an appropriate braid design, such as a closed-loop braid design, a single wire woven design, an endless braid design, or the like. The stent 100 of the illustrated embodiments is configured as a closed-loop braid design in which multiple strands are interlaced in a first direction (e.g., a distal direction) and then turn and are interlaced back in an opposite second direction (e.g., back in the proximal direction). The closed-loop braid design allows for fully automated or partially automated braiding (e.g., interlacing) of the multiple strands. In other embodiments, the stent 100 may be configured as a single wire woven design in which a single strand is woven (e.g., interlaced) with itself. It should be understood that when woven wires 160 are referenced herein that the ends of a single strand will overlap with itself. In still other embodiments, the stent 100 may have an endless braid design in which multiple strands are interlaced, generated, for example, by an automated process braiding in a single direction. An endless braid design may involve a braiding process that interlaces strands from one end to the other (e.g., does not involve a turn and return in the opposite direction). The endless braid design may involve more welds than the closed-loop braid design. A skilled artisan having the benefit of this disclosure can appreciate that a stent or implantable prosthesis of the present disclosure may have a construction of any of a single wire woven design, an endless braid design, or a closed-loop design and that such construction may utilize any suitable braid pattern.

The braided or woven wires 160 may include varying numbers of strands. For example, a smaller diameter stent, such as a 6 mm (based on the middle region 110 diameter), may include 24 strands (12 wires if a closed-loop braid design) and a larger diameter stent, such as a 20 mm, may include 64 strands (32 wires if a closed-loop braid design).

When braided or woven in a closed-loop braid design, the braided or woven wires 160 may start and stop at various locations on the stent 100. For example, individual braided wires 160 may be braided starting from the second flared end 130, through the middle region 110, through the first flared end 120, to the first opening 128, back through the first flared end 120, back through the middle region 110, and back through the second flared end 130. In other embodiments, the braided or woven wires 160 may start in the middle region 110.

Figure 6:
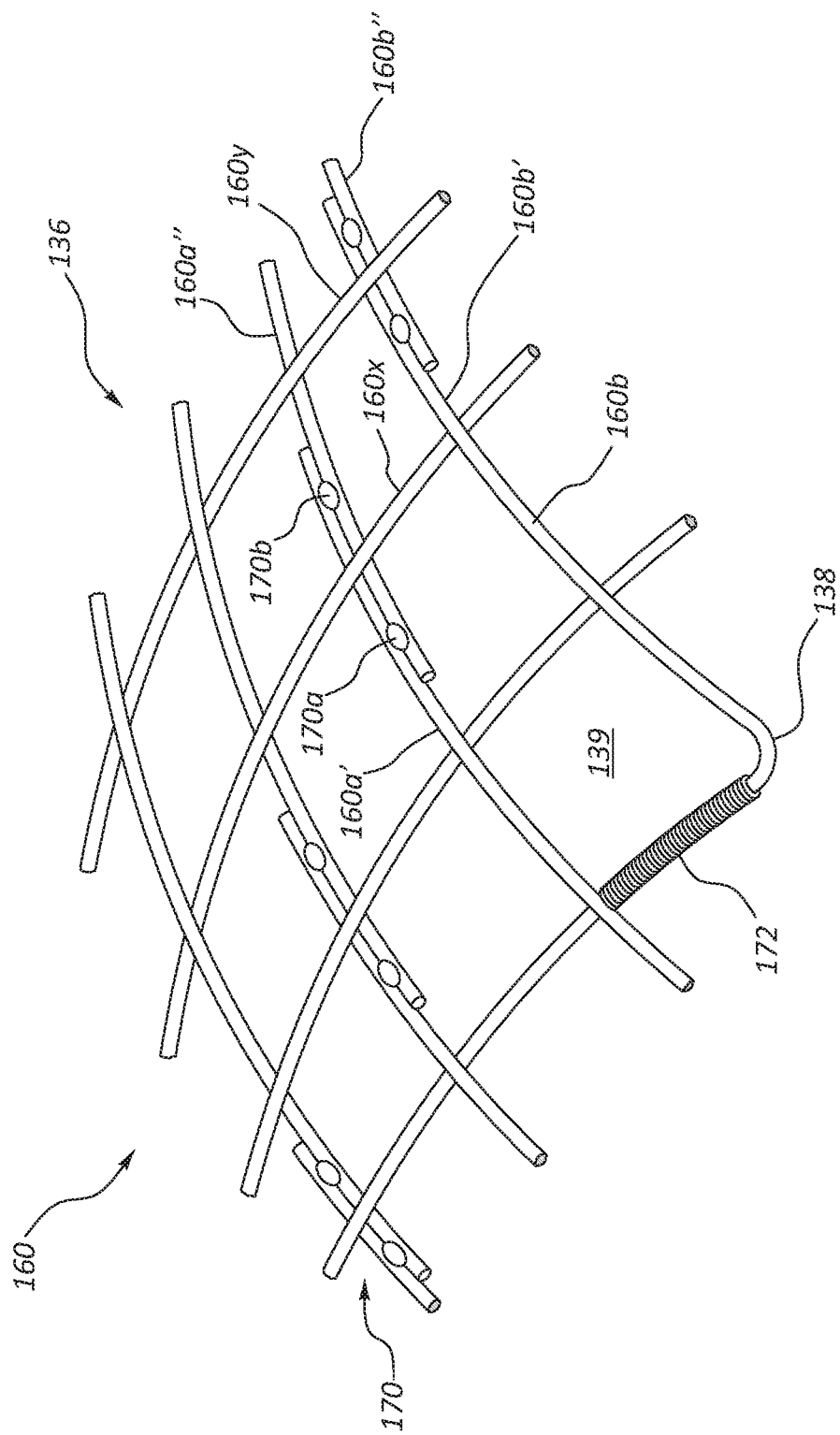
FIG. 6 illustrates one embodiment for forming wire end loops and joining wires for the exemplary embodiment of FIG. 1.

FIG. 6 illustrates such an example where the beginning and the end of each of the individual braided wires 160 overlap with other individual braided wires 160 underneath an intersecting strand along the second outer taper 136 and not at the second opening 138. For example, the second strand 160b is illustrated as bent about 90 degrees and then intersecting the first strand 160a. The interior region of the bent second strand 160b defines a second end loop 139 and the exterior defines a portion of the second opening 138.

FIG. 6 illustrates the use of spot welds 170 to secure each strand to another strand, such as the first strand 160a' to another strand 160a". In this embodiment, the overlap extends to either side of the intersection underneath the third intersecting strand 160x and the spot welds 170a and 170b are on either side the intersection. Other alternatives include increasing the length of the overlap and placing spot weld 170b on an opposing side of a second intersecting strand, such as the fourth intersecting strand 160y. Alternatively, the tension of the braid pattern may be used to secure the first strand 160a to itself, without spot welds 170. For example, as illustrated, a stub end 160b' of the bent second strand 160b resides on the interior of the joint with a long end 160b" of another strand. The tension of the joint helps hold the stub end 160b' in place. Moreover, the ends of the stands may be inserted into a sleeve and then the sleeve crimped (not shown). One of ordinary skill in the art, with the benefit of this disclosure, would understand that a variety of termination strategies may be used to secure the first strand 160a to itself (and likewise for securing two separate strands together). Securing the ends of the stands 160 to each other at a location other than the first and second openings 128 and 138 decreases strain on the joint, as compared, for example, to welding the ends to each other to form the second end loop 139. However, in some embodiments, the ends of the strands 160 may be welded to each other to form the first and second end loops 129 and 139.

Figure 6A:
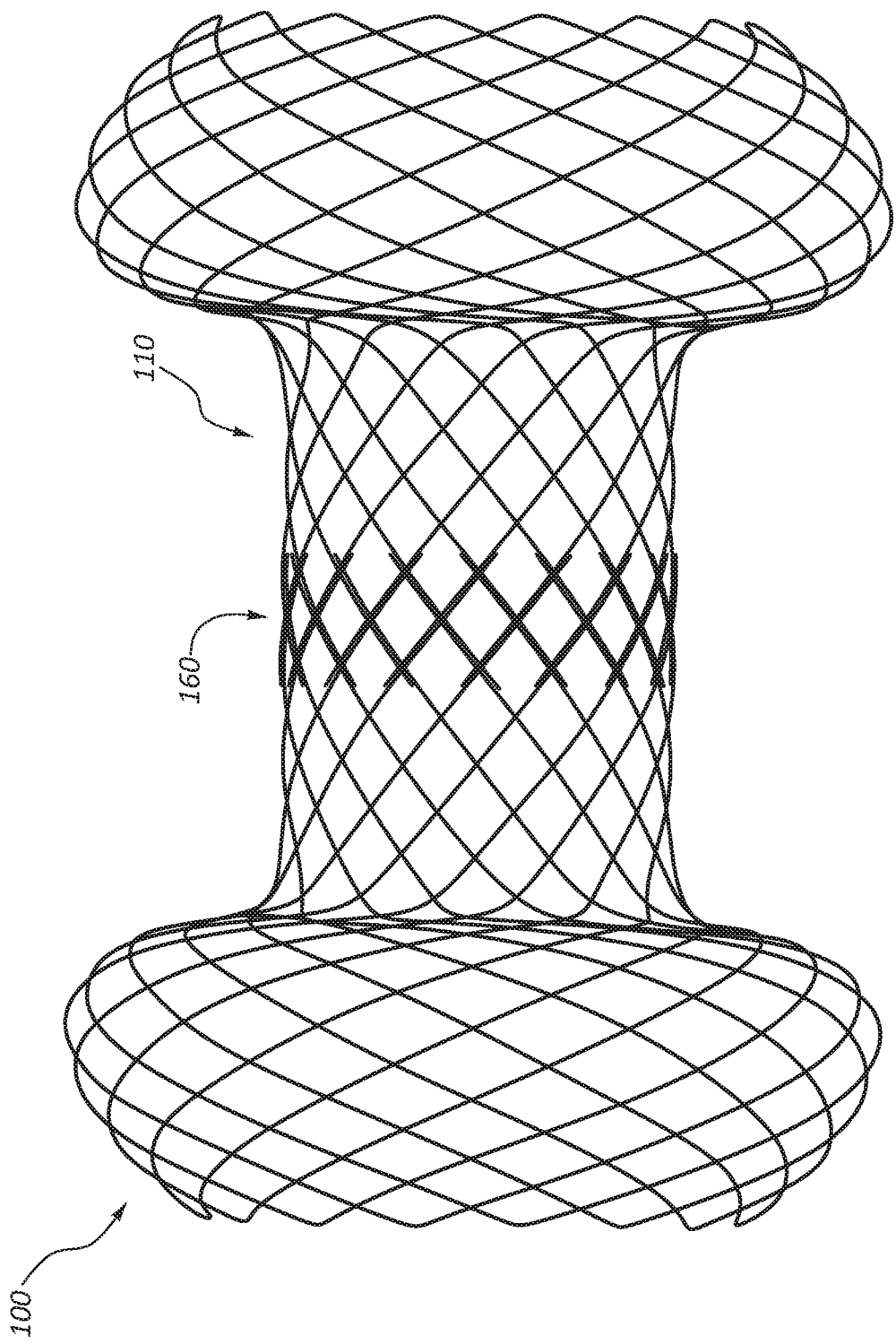
FIG. 6A illustrates an embodiment of braided or woven wires starting and terminating in a middle region of a stent.

FIG. 6A illustrates an embodiment of the braided or woven wires 160 starting and terminating in the middle region 110. Embodiments wherein the strand ends terminate anywhere within the middle region 110 and no strand ends are disposed within the first flared end 120 and the second flared end 130 are within the scope of this disclosure. The termination strategies discussed above with respect to terminating wires at the first and second outer tapers 126 and 136 apply to this embodiment as well.

FIG. 6 further illustrates a radiopaque coil 172 slid over the second strand 160b between the bend and the intersection with the first strand 160a. The radiopaque coil 172 may be locked in place by the bend and the intersection. The radiopaque coil 172 may also be placed in other locations, such as at the bend. The radiopaque coil 172 may comprise a tightly wound wire, such as a 25 micron wire. The wire may comprise platinum and tungsten or other radiopaque materials, such as platinum and iridium. The radiopaque coil 172 may be evenly spaced on the second end loops 139 circumscribing the second opening 138 and likewise for the first end loops 129 (see FIG. 7). A few of the radiopaque coils 172 may also be placed in the middle region 110. A number of alternatives to the radiopaque coils 172 exist, for example, the braided or woven wires 160 (or only a few of them) may be made of a radiopaque material, such as DFT wire with a nickel-titanium sheath with a platinum core.

The first end loops 129 may uniformly peak at the first end plane 127 (see FIGS. 2 and 5) and the second end loops 139 uniformly peak at the second end plane 137 (see FIGS. 3 and 5). Alternatively, the first and second end loops 129 and 139 may be staggered, such as illustrated in FIG. 7 for the first end loops 129" of the stent 100". It should be understood that the disclosure regarding the stent 100 applies equally to the stent 100" and vice versa.

The braided or woven wires 160 forming the stent 100 may comprise any suitable material known in the art, including plastics and memory alloys. In some embodiments, the braided or woven wires 160 may be Nitinol, including ASTM F2063. In one embodiment, the thickness of a memory alloy strand of the braided or woven wires 160 may be about 0.003 in. to about 0.009 in. In other embodiments, the thickness may be about 0.005 in. to about 0.065 in., such as for about 6 mm to about 20 mm in diameter (middle region 110) stents. Generally speaking, smaller wires may be used with smaller diameter stents and larger diameter wires may be used with larger diameter stents.

FIG. 7 illustrates that the stent 100" further includes a cover 180" coupled to the braided or woven wires 160". The cover 180" can further define the interior dimension 102" and the outer dimension 103". The cover 180" may be elastomeric, polymeric, or comprised of any other material known in the art. In some embodiments, the cover may include silicone, while in certain embodiments the cover may be comprised only of silicone, such as Nusil MED-4055 for short-term implants or MED-4755 for long-term implants. 55 durometer and higher silicones may facilitate crimping into low-profile catheters, such as a 10.8 French sized catheter.

In some embodiments, the cover 180 (see FIG. 5) may be applied such that it tends to ebb and flow into spaces between portions of the braided or woven wires 160, resulting in a "tire tread" like outer surface, rather than a smooth outer cover. In some embodiments such a design may be configured to allow tissue to lock into the uneven spaces and treads, thus adding anti-migration properties in some instances.

In some embodiments the cover 180 may include multiple subparts or layers. For example, in some embodiments the cover 180 may be a two-part design. Such two-part covers may be composed of a base cover which encapsulates the braided or woven wires 160 and a second cover which may be applied after the first cover cures. In certain embodiments, the second cover may only be applied to the outside diameter of the stent 100 and may chemically bond to the first cover layer. Multiple-layered covers may be configured such that the primary layer adds elasticity or resiliency to the stent while the second, outer layer reduces friction along the outside diameter. Manufacturing aids, such as MED-400 silicone, may be present as well. Manufacturing aids may help with crimping and loading, reduce deployment force, and increase the shelf life of the stent 100. It is within the scope of this disclosure to use any of the exemplary materials for any of the layers.

In FIG. 7, the cover 180" extends beyond the first end loops 129", further narrowing the circumference of the first opening 128". In such embodiments, the cover 180" may extend about 0.2 mm to about 1 mm beyond the wires.

Regarding manufacturing of the stent 100, initially, a first mandrel (not shown) may be used. The first mandrel may have an outer cylindrical surface with a constant cylindrical shape and have a diameter equal to the diameter of the middle region 110 of the stent 100. The braided or woven wires 160 (when they constitute a shape-memory material) may be braided or woven so as to have a first end region, a middle region, and a second end region along the first mandrel. The middle region may have a constant pitch and the first and second end regions may have continuously varying pitches.

Figure 5B:
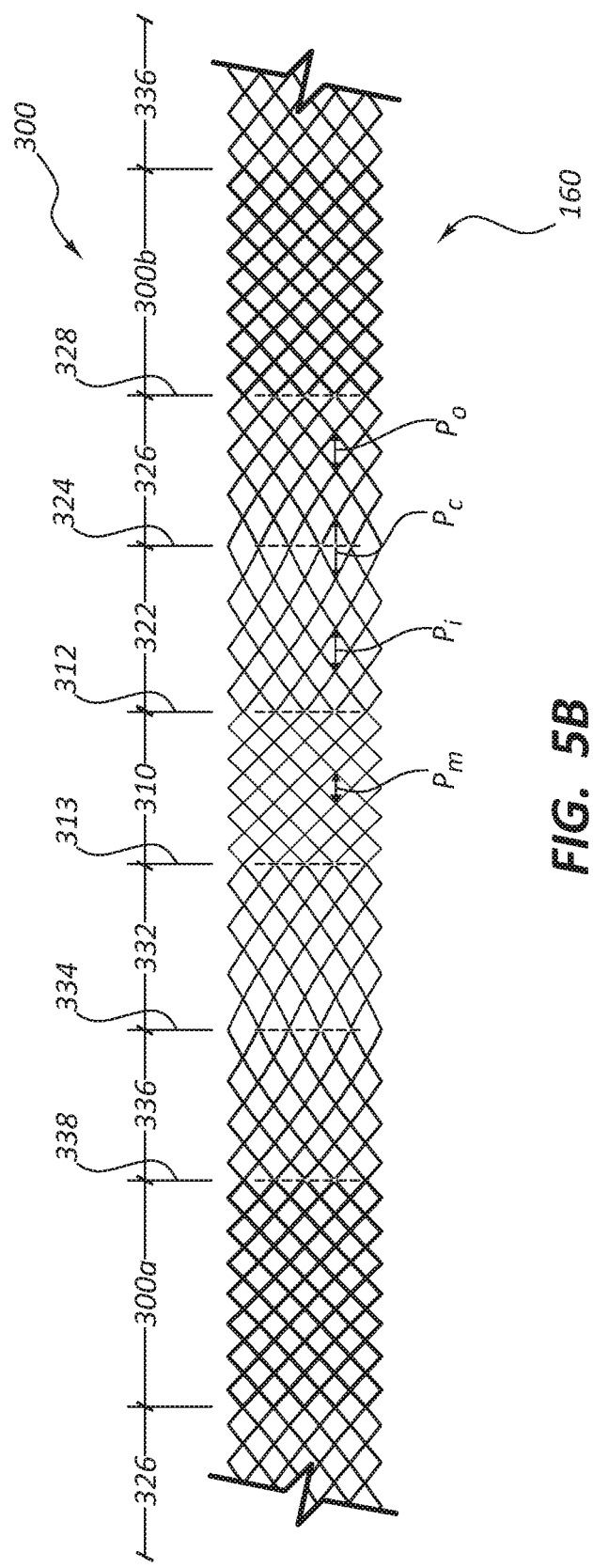
FIG. 5B illustrates various pitches of different regions of the stent.

FIG. 5B illustrates an example of the various pitches that may be braided or woven onto the first mandrel to achieve the pitches of the stent 100 when the stent 100 is stretched into final form. FIG. 5B illustrates continuous wires 300 that may be used for providing the braided or woven wires 160. Starting from the middle, region 310 corresponds to middle region 110 of the stent 100. Region 322 corresponds to the first inner shoulder 122 of the stent 100. Region 332 corresponds to the second inner shoulder 132 of the stent 100. Region 326 corresponds to the first outer taper 126 of the stent 100. Region 336 corresponds to the second outer taper 136 of the stent 100. Likewise, line 312 corresponds to the proximal end 112 of the middle region 110 and line 313 corresponds to the distal end 113. Line 324 corresponds to the first crest 124 and line 334 corresponds to the second crest 134. Line 328 corresponds to the first opening 128 and line 338 corresponds to the second opening 138. Regions 300a and 300b facilitate manufacturing and separate one set of braided or woven wires 160 from a second set of braided or woven wires 160.

When braided or woven onto the first mandrel, the Pm may be constant and may be the same as it will be in the stent 100; however, the Pi, Pc, and Po are not. The Pc is greater than the Pi and Po, which are both greater than the Pm. Once formed into the stent 100, the Pc will be less than the Pm, as discussed previously.

FIG. 8 illustrates a second mandrel 200 for use in manufacturing the stent 100. The second mandrel 200, when assembled, matches the shape of the stent 100. The second mandrel 200 includes two parts, a first end 200a and a second end 200b. The second mandrel 200, when assembled, includes a middle cylindrical region 210 that matches the diameter of the middle region 110 of the stent 100. Likewise, the first part 200a includes a first flared end 220 that matches the shape of the first flared end 120. The second part 200b includes a second flared end 230 that matches the shape of the second flared end 130. The second part 200b includes a plug 201 for insertion into a receiver 202 of the first part 200a. One of skill in the art, with the benefit of this disclosure, would understand that a variety of structures and approaches may be used to connect the first part 200a to the second part 200b.

A set of braided or woven wires 160 is cut in the regions 300a and 300b to separate it from the continuous wires 300. The braided or woven wires 160 may then be removed from the first mandrel. The first and second parts 200a and 200b may be slid into the braided or woven wires 160 until the first and second parts 200a and 200b are joined together. Regions 310, 322, 326, 332 and 336 may then be aligned over the middle region 210, the first flared end 220, and the second flared end 230 of the second mandrel 200. The pitches of Pi, Pc, and Po change as the braided or woven wires 160 are slid in place over the second mandrel 200. The braided or woven wires 160 are then set in place, such as with heat.

After being heat-set, for example, the braided or woven wires 160 may be removed from the second mandrel 200. The second mandrel 200 may be separated into two parts and removed from inside the stent 100. The Po pitch allows the braided or woven wires 160 to scissor sufficient to allow removal of from the first and second parts of the second mandrel 200 without damage.

The braided or woven wires 160 may then be placed on a third mandrel that is the same shape as the mandrel 200 for coating. The third mandrel may be polished to thereby leave a surface roughness on the cover 180 equal to or less than 2 Ra (arithmetic average of roughness profile). As with the second mandrel 200, the Po pitch allows the braided or woven wires 160 to scissor sufficient to allow removal of from the first and second parts of the third mandrel without damage.

The stents disclosed herein, such as the stent 100, may be used for draining one lumen of a patient into another lumen of a patient, such as, for example, transgastric or transduodenal drainage of a pancreatic pseudocyst, of a biliary tract, of a gallbladder. An access port may be created between a first lumen of the patient and a second lumen of the patient. For examples, NOTES (natural orifice transluminal endoscopic surgery) may be used to create the access port between the lumens. The first lumen may be the gastrointestinal tract (for example, the esophagus, stomach, pylorus, or bowel) of the patient. The second lumen may be the gallbladder, a pancreatic cyst, a biliary tract, or some other lumen that needs drainage. A delivery catheter with the stent loaded in an elongated and stretched state may be introduced through the working channel of an echoendoscope or other device. The second flared end (in its stretched and elongated state) may be introduced through the access port into the second lumen and then the second flared end released so that the second flared end is secured against a luminal wall of the second lumen. The first flared end can then be released so that the first flared end is secured against a luminal wall of the first lumen. In its unstretched and unelongated state, the interior dimension of the stent provides fluidic communication between the first and second lumens. The second lumen can passively drain into the first lumen or the second lumen can be actively drained by insertion of other tools through the interior dimension into the second lumen to remove material from the second lumen (such as, for example, gallstones or malignant or necrotic tissue).

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, only a portion of a method described herein may be a separate method. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of this disclosure.

The invention claimed is:

1. A method of using a stent, comprising:
    obtaining a stent comprising:
        a hollow cylindrical body having an interior dimension and an exterior dimension and comprising a middle region that extends to a first flared end and also extends to an opposing second flared end,
        the first flared end comprising a first inner shoulder, a first crest, a first outer taper, and a first opening, wherein the first inner shoulder extends from one end of the middle region to the first crest, wherein a diameter of the first crest is greater than a diameter of the middle region, wherein the first outer taper extends from the first crest to the first opening, wherein the first opening provides a first boundary between the interior dimension and the exterior dimension,
        the hollow cylindrical body characterized by a longitudinal plane that bisects the hollow cylindrical body along its longitudinal axis, characterized by a first perpendicular plane that encompasses a circle defined by the first crest, and wherein the first perpendicular plane is perpendicular to the longitudinal plane,
        wherein a profile of at least a portion of the first inner shoulder, the first crest, and at least a portion of the first outer taper circumscribes a portion of a first elliptical arc of a first ellipse that lies in the longitudinal plane, wherein the first elliptical arc includes an upper antipodal point of the first ellipse, wherein a lower antipodal point of the first ellipse is outwardly offset along the longitudinal plane relative to the first perpendicular plane and the middle region; and delivering the stent into a body lumen of a patient, wherein delivering the stent into the body lumen comprises delivering the first flared end of the stent into a portion of a gastrointestinal tract of the patient, wherein the portion of the gastrointestinal tract comprises an esophagus.

2. The method of claim 1, wherein delivering the stent into the body lumen further comprises:
    delivering the second flared end of the stent into a second body lumen of the patient.

3. The method of claim 1, wherein obtaining the stent comprises obtaining the stent loaded in a delivery catheter in an elongated and stretched state.

4. The method of claim 1, wherein the second flared end comprises a second inner shoulder, a second crest, a second outer taper, and a second opening, wherein the second inner shoulder extends from one end of the middle region to the second crest, wherein a diameter of the second crest is greater than a diameter of the middle region, wherein the second outer taper extends from the second crest to the second opening, wherein the second opening provides a second boundary between the interior dimension and the exterior dimension,
    wherein the hollow cylindrical body is further characterized by a second perpendicular plane that encompasses a circle defined by the second crest, the second perpendicular plane also perpendicular to the longitudinal plane, and
    wherein a profile of at least a portion of the second inner shoulder, the second crest, and at least a portion of the second outer taper circumscribes a portion of a second elliptical arc of a second ellipse that lies in the longitudinal plane, wherein the second elliptical arc includes an upper antipodal point of the second ellipse, wherein a lower antipodal point of the second ellipse is outwardly offset along the longitudinal plane relative to the second perpendicular plane and the middle region.

5. The method of claim 1, wherein a diameter of the first opening is greater than the diameter of the middle region, but less than the diameter of the first crest.

6. The method of claim 1, wherein the first inner shoulder comprises a first perpendicular region concentrically surrounding and perpendicular to the middle region.

7. The method of claim 6, wherein the first elliptical arc extends from the first perpendicular region, along the first crest, and along the first outer taper to the first opening.

8. The method of claim 1, wherein the lower antipodal point of the first ellipse is outwardly offset along the longitudinal plane relative to the first perpendicular plane and the middle region by about 5 degrees to about 60 degrees.

9. A method of using a stent comprising:
    obtaining a stent comprising:
        a hollow cylindrical body having an interior dimension and an exterior dimension and comprising a middle region that extends to a first flared end and also extends to an opposing second flared end,
        the first flared end comprising a first inner shoulder, a first crest, a first outer taper, and a first opening, wherein the first inner shoulder extends from one end of the middle region to the first crest, wherein a diameter of the first crest is greater than a diameter of the middle region, wherein the first outer taper extends from the first crest to the first opening, wherein the first opening provides a first boundary between the interior dimension and the exterior dimension, the second flared end comprising a second inner shoulder, a second crest, a second outer taper, and a second opening, wherein the second inner shoulder extends from one end of the middle region to the second crest, wherein a diameter of the second crest is greater than a diameter of the middle region, wherein the second outer taper extends from the second crest to the second opening, wherein the second opening provides a second boundary between the interior dimension and the exterior dimension, the hollow cylindrical body comprising braided or woven wires having a constant pitch along a length of the middle region, the braided or woven wires having a uniformly varying pitch along the first inner shoulder, the braided or woven wires having a constant pitch at the first crest, the braided or woven wires having a uniformly varying pitch along the first outer taper, the braided or woven wires having a uniformly varying pitch along the second inner shoulder, the braided or woven wires having a constant pitch at the second crest, and the braided or woven wires having a uniformly varying pitch along the second outer taper; and delivering the stent into a body lumen of a patient, wherein delivering the stent into the body lumen comprises delivering the first flared end of the stent into a portion of a gastrointestinal tract of the patient, wherein the portion of the gastrointestinal tract comprises an esophagus.

10. The method of claim 9, wherein delivering the stent into the body lumen further comprises:

delivering the second flared end of the stent into a second body lumen of the patient.

11. The method of claim 9, wherein obtaining the stent comprises obtaining the stent loaded in a delivery catheter in an elongated and stretched state.

12. The method of claim 9, wherein the uniformly varying pitch along the first and second inner shoulders is continuously decreasing from the middle region to the first and second crests, respectively.

13. The method of claim 9, wherein the uniformly varying pitch along the first outer taper is continuously increasing from the first crest to the first opening and wherein the uniformly varying pitch along the second outer taper is continuously increasing from the second crest to the second opening.

14. The method of claim 9, wherein the uniformly varying pitch along the first outer taper is configured to allow the braided or woven wires at the first opening to expand equal to the diameter of the first crest and wherein the uniformly varying pitch along the second outer taper is configured to allow the braided or woven wires at the second opening to expand equal to the diameter of the second crest.

15. A method of using a stent comprising:

obtaining a stent loaded in a delivery catheter in an elongated and stretched state, the stent comprising:

a hollow cylindrical body having an interior dimension and an exterior dimension and comprising a middle region that extends to a first flared end and also extends to an opposing second flared end, the first flared end comprising a first inner shoulder, a first crest, a first outer taper, and a first opening, wherein the first inner shoulder extends from one end of the middle region to the first crest, wherein a diameter of the first crest is greater than a diameter of the middle region, wherein the first outer taper extends from the first crest to the first opening, wherein the first opening provides a first boundary between the interior dimension and the exterior dimension, the second flared end comprising a second inner shoulder, a second crest, a second outer taper, and a second opening, wherein the second inner shoulder extends from one end of the middle region to the second crest, wherein a diameter of the second crest is greater than a diameter of the middle region, wherein the second outer taper extends from the second crest to the second opening, wherein the second opening provides a second boundary between the interior dimension and the exterior dimension; and delivering the first flared end of the stent into a portion of a gastrointestinal tract of a patient, wherein the portion of the gastrointestinal tract comprises an esophagus.

* * * * *